(12) United States Patent
Nakashige et al.

(10) Patent No.: US 7,010,430 B2
(45) Date of Patent: Mar. 7, 2006

(54) METHOD FOR DISPLAYING GENE EXPERIMENT DATA

(75) Inventors: Ryo Nakashige, Kanagawa (JP); Yasuyuki Nozaki, Kanagawa (JP); Takuro Tamura, Kanagawa (JP); Tsunehiko Watanabe, Kanagawa (JP)

(73) Assignee: Hitachi Software Engineering Co., Ltd., Kanagawa (JP)

( * ) Notice: Subject to any disclaimer, the term of this patent is extended or adjusted under 35 U.S.C. 154(b) by 435 days.

(21) Appl. No.: 09/819,179

(22) Filed: Mar. 27, 2001

(65) Prior Publication Data

US 2002/0049543 A1   Apr. 25, 2002

(30) Foreign Application Priority Data

| Mar. 27, 2000 | (JP) | 2000-086818 |
| Sep. 14, 2000 | (JP) | 2000-280052 |

(51) Int. Cl.
*G06F 17/11* (2006.01)
*G06G 7/58* (2006.01)
*G06N 7/00* (2006.01)

(52) U.S. Cl. .......................................... 702/19; 703/2
(58) Field of Classification Search ................. 702/19, 702/20, 27; 703/11
See application file for complete search history.

(56) References Cited

U.S. PATENT DOCUMENTS 5,986,673 A   11/1999   Martz

FOREIGN PATENT DOCUMENTS

EP   0 738 990 A2   4/1996

OTHER PUBLICATIONS

Schena et al., Proceedings of the National Academy of Sciences (USA), vol. 93, pp. 10614-10619 (1996).*

(Continued)

*Primary Examiner*—Marjorie A. Moran
*Assistant Examiner*—Marina Miller
(74) *Attorney, Agent, or Firm*—Reed Smith LLP; Stanley P. Fischer, Esq.; Juan Carlos A. Marquez, Esq.

(57) ABSTRACT

The present invention aims at providing a visual display which is useful in roughly understanding the state of groupings and changes, by comparing expression data of genes from two experiments based on expression data of one sample common to both experiments.

In order to compare data of expression levels obtained from different experiments each using two types of samples, three types of expression levels are displayed in three-dimension as mediated by the data of the common sample used in both experiments. Specifically, expression level data for Samples A and B and expression level data for Samples A and C are combined and converted into single three-dimensional data and displayed as points inside a sphere. Alternatively, expression states of each gene to Samples A, B and C are mapped on a sphere with respect to a ratio between Sample A and Sample B and a ratio between Samples A and C, and displayed as distribution on the surface of the sphere. A clustering analysis is performed based on the distributed points inside or on the sphere, to visually understand the expression state of genes for the three types of samples. In addition, the expression level data displayed as points inside or on the sphere are linked as a line or a curve for each gene or for each gene group resulting from the clustering analysis, to visually understand the changes of expression states with time.

9 Claims, 13 Drawing Sheets

OTHER PUBLICATIONS

Javed Khan et al, "Gene Expression Profiling of Alveolar Rhabdomyosarcoma with cDNA Microarrays", Cancer Research 58 (Advances in Brief), Nov. 13, 1998, pp. 5009-5013.

A. Alizadeh et al., "The Lymphochip: A Specialized cDNA Microarray for the Genomic-Scale Analysis of Gene Expression in Normal and Malignant Lymphocytes", (1999), Cold-Spring Harbor Symposium on Quantitative Biology, vol. LXIV, pp. 71-78.

F. Guyon et al., "Mappetshow: Non-Linear Visualization for Genome Data", Pacific Symposium on Biocomputing, Jan. 4, 2000, pp. 206-217, 12 pages.

Bernd Meyer, "Self-Organizing Graphs—A Neural Network Perspective of Graph Layout", 1998, Lecture Notes in Computer Science, vol. 1547, 1998, pp. 246-262.

* cited by examiner

FIG. 5

|         | Experiment 1 ||  | Experiment 2 ||
| Gene ID | Normal A | Disease B | | Normal A | Disease C |
|---|---|---|---|---|---|
| 1 | 1,234 | 56 | | 1,025 | 72 |
| 2 | 11,224 | 888 | | 336 | 7,728 |
| 3 | 107 | 3,408 | | 10,043 | 298 |
| ⋮ | ⋮ | ⋮ | | ⋮ | ⋮ |
| m | 9,753 | 8,905 | | 7,531 | 6,907 |

METHOD FOR DISPLAYING GENE EXPERIMENT DATA

FIELD OF THE INVENTION

The present invention relates to a method for displaying gene expression data obtained from two types of experiments by hybridization with particular genes, in a visually understandable manner to aid prediction of a function and a role of the gene.

BACKGROUND OF THE INVENTION

With the increase in the number of species that have been determined of their genome sequences, so called genome comparison has extensively been performed. Genome comparison aims at finding facts based on gene differences among species, for example, finding genes involved in evolution, finding a collection of genes which are considered to be common to all species, or, on the other hand, studying the nature unique to specific species. The recent development of infrastructures such as biochips (DNA chips) and DNA microarrays has changed the interest in the art of molecular biology from information of interspecies to information of intraspecies, namely coexpression analysis, and broadened the study covering from extraction of information to correlation of information, in addition to the conventional comparison between species.

For example, if an unknown gene has an expression pattern identical to that of a known gene, the unknown gene can be assumed to have a similar function to that of the known gene. Functional meanings of such genes and proteins are studied in the forms of function units or function groups. The interactions between the function units or function groups are also analyzed by correlating with known enzymatic reaction data or metabolism data, or more directly, by knocking out or overreacting a specific gene to eliminate or accelerate expression of the gene to study the direct and indirect influences on gene expression patterns of a whole collection of genes.

One successful case in this field would be the expression analysis of yeast by the group of P. Brown et al. from the Stanford University (Michel B. Eisen et al., Clustering analysis and display of genome-wide expression patterns, *Proc. Natl. Acad. Sci.* (Dec. 8, 1998); 95(25): pp. 14863–8). They conducted hybridization of genes extracted from a cell in a time series using a DNA microarray, and numerically expressed the expression levels thereof (i.e., the brightness of the hybridized fluorescent signals). Based on the numerically-expressed values, genes having similar expression patterns in their gene cycles (genes having closer expression levels at some point) are clustered together.

Furthermore, experimental results as to an efficacy of a medicine has been reported by The Institute of Medical Science, the University of Tokyo (T. Tsunoda et al., Discrimination of Drug Sensitivity of Cancer Using cDNA Microarray and Multivariate Statistical Analysis: Genome Informatics 1999 (December 1999) pp.227–228, Universal Academy Press Inc.). In the experiment, a normal cell sample and a cancer cell sample which are labeled with fluorescent substances with different colors are subjected to hybridization on a biochip. Then, both of the fluorescent signal intensities are measured.

FIG. 3 is a diagram for illustrating an exemplary method for displaying an expression state of each gene obtained from the experiment. In this display, data of brightness of hybridized fluorescent signals are plotted, where one axis represents brightness of a normal cell and the other brightness of a cancer cell. In order to analyze the data, a ratio of brightness of the cancer cells to that of the normal cell is observed for genes having signals higher than a predetermined intensity, thereby narrowing the number of candidate genes specific to a disease. Specifically, genes belonging to Region A in FIG. 3 (genes that function for the normal cell but for the cancer cell) and genes belonging to Region B (genes that function for the cancer cell but for the normal cell) are particularly sorted. According to such a displaying method, the number of candidate genes that act specific to a particular disease can be narrowed down.

The displaying method shown in FIG. 3 is effective in visually understanding rough difference between properties of genes in different, cells, and is currently used as a general method. According to this method, the number of samples to be compared is limited to two. However, in analyzing functions of genes, there is a demand of analyzing various cells suffering from diseases from various points of view, for example, as to genes specific to one or more diseases, or genes that function only under a normal condition. Therefore, a displaying method that is limited to two types of samples is not always satisfactory.

For example, where three types of cells, Normal cell A, Cell B suffering from Disease P and Cell C suffering from Disease Q are to be compared, experiments should be carried out for each two of them. Therefore, two of the displays like one shown in FIG. 3 are obtained as the experiment results. Specifically, one of the two displays may be for the results of an experiment targeting Normal cell A and Cell B suffering from Disease P, and the other for the results of an experiment targeting Normal cell A and Cell C suffering from Disease Q. Based on the experiment results of one of the cells, other two types of cells can be compared with each other. However, even when the two displays like one shown in FIG. 3 are placed side by side, it is hard to understand the states of gene expressions of these three cells by a brief look.

In general, in order to study expression states of a gene, an experiment using a biochip is carried out at each time point, to understand changes of various genes by displaying expression data of each gene in a time series. FIGS. 9A and 9B are representative graphs. FIG. 9A is a graph showing changes of an expression level of one gene (Gene 1) with time. FIG. 9B is a graph collectively showing changes of multiple genes with time. From the graph shown in FIG. 9B, it can be predicted that in a region (900) enclosed with a circle, Genes 1, 2 and 3 are working in cooperation within a predetermined time segment.

However, it is difficult to apply this graph displaying method to the above-described data obtained by observing the ratios of expression levels among the three types of cells, to roughly understand the states of entire changes as to how the gene expressions are related to each other.

In view of such conventional problems, the present invention has an objective of providing a visual display effective in comparing expression data of multiple gene based on experiment results of one type of cell to understand states of groupings and changes.

SUMMARY OF THE INVENTION

To achieve the above-mentioned objective, the present invention is carried out as follows. In order to compare data of expression levels obtained from different experiments using each two types of samples, expression levels of genes for three types of samples are displayed in three-dimension as mediated by the data of the common sample used in both experiments. Specifically, data of expression levels of genes for Samples A and B and data of expression levels of genes for Samples A and C are combined and converted into single three-dimensional data as mediated by the expression levels of genes for Sample A, and displayed as points inside a sphere. Alternatively, expression states of each gene for Samples A, B and C are mapped on a surface of a sphere with respect to a ratio of expression levels of genes between Samples A and B and a ratio of expression levels of genes between Samples A and C, and displayed as distribution on a sphere. By performing a clustering analysis based on the distributed points in or on the sphere, the expression states of genes for the three types of samples can visually be understood.

A method for displaying gene expression data according to the present invention, comprises combining expression level data of a plurality of genes from an experiment using Samples A and B and expression level data of a plurality of genes from an experiment using Samples A and C, as mediated by the expression level data of genes for Sample A which is commonly used in both experiments; and displaying the results of the combination.

In an experiment using Samples A and B for acquiring expression level data of a plurality of genes for Samples A and B, a mixture of equal amounts of Samples A and B is preferably acted against each gene to equalize experiment conditions for both Samples A and B. Similarly, in an experiment using Samples A and C for acquiring expression level data of a plurality of genes for Samples A and C, a mixture of equal amounts of Samples A and C is preferably acted against each gene to equalize experiment conditions for both Samples A and C. The amounts of Samples A and B, or the amounts of Samples A and C which have been hybridized to each gene can be detected, for example, by labeling Samples A and B with distinct fluorescence substances and labeling Samples A and C with distinct fluorescence substances.

The expression level data of the plurality of genes for Samples A and B, and those for Samples A and C resulting from the two experiments can be combined and displayed as mediated by the expression level data of genes for Sample A. In this displaying method, for example, two-dimensional display may be employed where the x-axis represents a gene expression level for Sample B while the y-axis represents a gene expression level for Sample C. According to this displaying method, expression states of each gene for Samples B and C can visually be observed although Samples B and C are not subjected to an experiment together.

Alternatively, the above-described displaying method may comprise displaying the expression level data of the plurality of genes by taking expression levels of the genes for Samples A, B and C on the x-, y- and z-axes, respectively. According to this method of three-dimensional display, expression states of each gene toward three types of samples can be observed at a glance, and grouping of similar genes is easy.

When the gene experiment data is displayed in three-dimension, the expression level data of the genes from the two experiments may be combined such as to conserve a ratio of the expression levels of each gene between Samples A and B and a ratio of the expression levels of each gene between Samples A and C; and the results obtained by the combination may be displayed on a surface of a sphere. The genes displayed on the sphere may further be subjected to a clustering analysis based on their displayed positions, and the gene groups resulting from the clustering analysis may be displayed as regions on the sphere.

Furthermore, the expression level data of the genes from the two experiments may be combined such as to conserve the magnitude relation of the expression levels of each gene between Samples A and B and the magnitude relation of the expression levels of each gene between Samples A and C, as well as to conserve a ratio of the expression levels of each gene between Samples A and B and a ratio of the expression levels of each gene between Samples A and C; and the results obtained by the combination may be displayed inside a sphere. Preferably, the displayed sphere is semi-transparent so that the points of data inside the sphere are visible. In this case, a clustering analysis may be performed based on the three-dimensional position of each gene displayed inside the sphere; and a gene group obtained by the clustering analysis may be displayed as a region inside the sphere.

In the above-described method for displaying gene experiment data, the expression level data is data in a time series, which is advantageously displayed based on the expression level data at respective time points for each gene such that the direction of the changes of the coordinate positions with time can be understood.

As the coordinate positions are displayed on the surface of the sphere, arrows or the like may be used to link the coordinate positions on the sphere to show the direction with the lapse of time. On the other hand, as the coordinate positions are displayed inside the sphere, arrows or the like may be used to link the three-dimensional coordinate positions inside the sphere. Accordingly, the display positions for Samples A, B and C inside the sphere or on the surface of the sphere may be traced for each gene as a line or a curve based on its expression level data measured in time series, thereby displaying the states of gene expressions in a time series.

In the above-described method for displaying gene experiment data, the expression level data may be data in a time series, and it is advantageous to display changes of regions with time resulting from the clustering analysis.

The changes of the regions with time may be displayed, for example, as travel, division or joining of the regions. When the gene groups resulting from the clustering analysis are displayed as regions on the surface of the sphere, the changes thereof with time are displayed as travel, division or joining of the regions on the sphere. Similarly, when the gene groups resulting from the clustering analysis are displayed as regions inside the sphere, and the changes thereof with time are displayed as travel, division or joining of the regions inside the sphere. According to this displaying method, in studying a plurality of genes together, the time path of the gene groups displayed on the surface of the sphere or inside the sphere may be calculated with the lapse of time to draw travel, division or joining of the gene groups, thereby displaying the changes of states of gene expression with time.

According to the present invention, experiment data of expressions of a plurality of genes can be displayed in a visually understandable manner where the functions and/or roles of the genes can easily be predicted.

BRIEF DESCRIPTION OF THE DRAWINGS

FIG. 5 is a diagram showing a specific example of gene expression data obtained from experiments.

DETAILED DESCRIPTION OF THE INVENTION

Hereinafter, embodiments of the present invention will be described with reference to the drawings.

Figure 1:
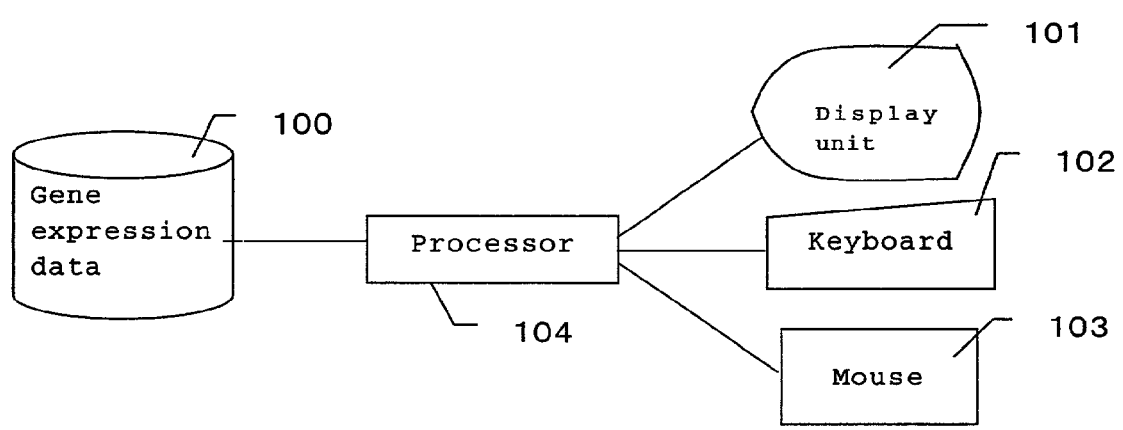
FIG. 1 is a schematic view showing a configuration of a system.

FIG. 1 is a schematic view showing a configuration of a system of the present invention. The system of the invention is provided with gene expression data 100 for storing numerically-expressed gene expressions levels in a series of cell process, a display unit 101 for visualizing and displaying the expression data, inputting devices such as a keyboard 102 and a mouse 103 for inputting values into the system and for selection, and a processor 104 for performing clustering of the expression data or the like with respect to the expression level of the gene.

Figure 2:
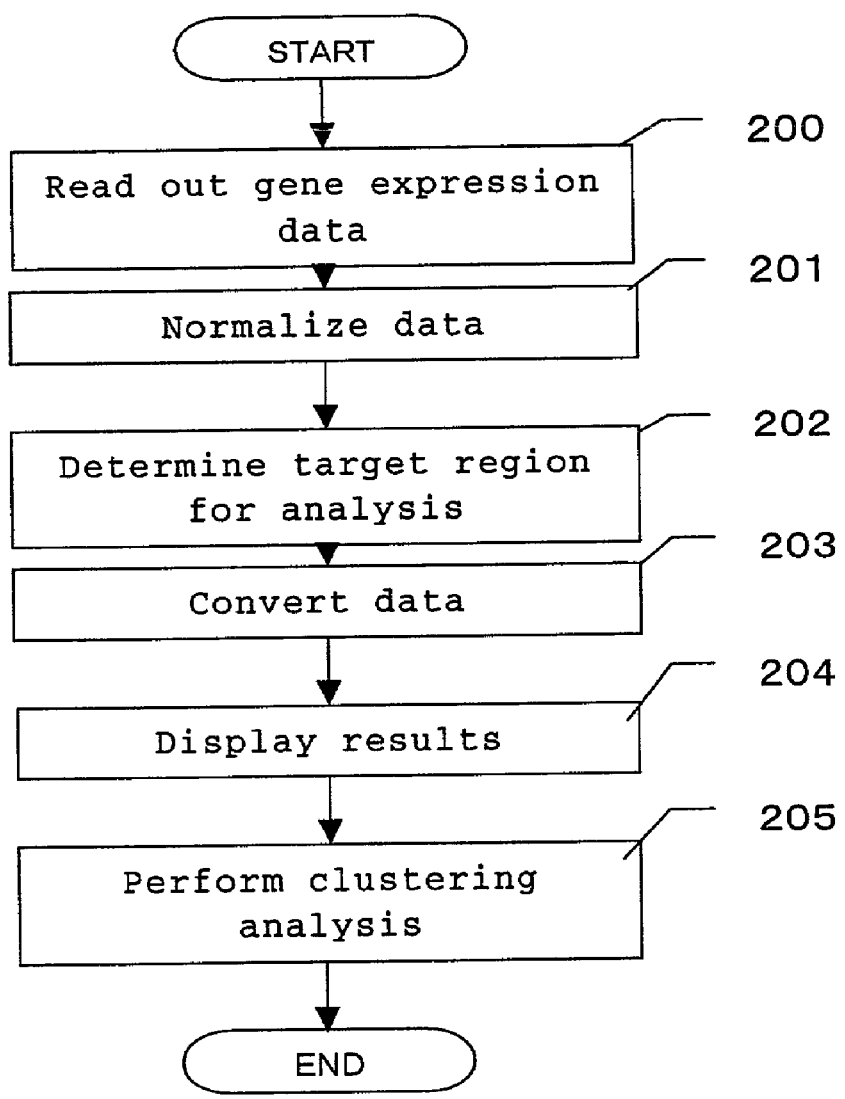
FIG. 2 is a flowchart showing general processes.

FIG. 2 is a flowchart showing general processes of a gene experiment data displaying method according to the present invention. Hereinafter, the processes will be described by following this flowchart.

First, data is read out from the gene expression data 100 and input into the processor 104 (Step 200). FIG. 5 shows specific examples of individual gene expression data as the results of the experiments. Exemplary results from the two experiments are shown. In Experiment 1, Normal cell A is compared with Cell B suffering from disease P. In Experiment 2, Normal cell is compared with Cell C suffering from disease Q. The results from each experiment are collectively represented in a table showing the expression levels (measured fluorescent brightness from a fluorescent substance labeling each cell) using gene ID as index. For example, the table shows that, for a gene assigned Gene ID 1 in Experiment 1, brightness of Fluorescent color R labeling Normal Cell A was measured 1,234 upon a hybridization reaction on a biochip, while brightness of a Fluorescent color G labeling Cell B suffering from disease P was measured 56. Although the total number of the target genes varies depending on the experiment, the total number of genes is acceptable to an order of hundreds to ten-thousands.

Figure 3:
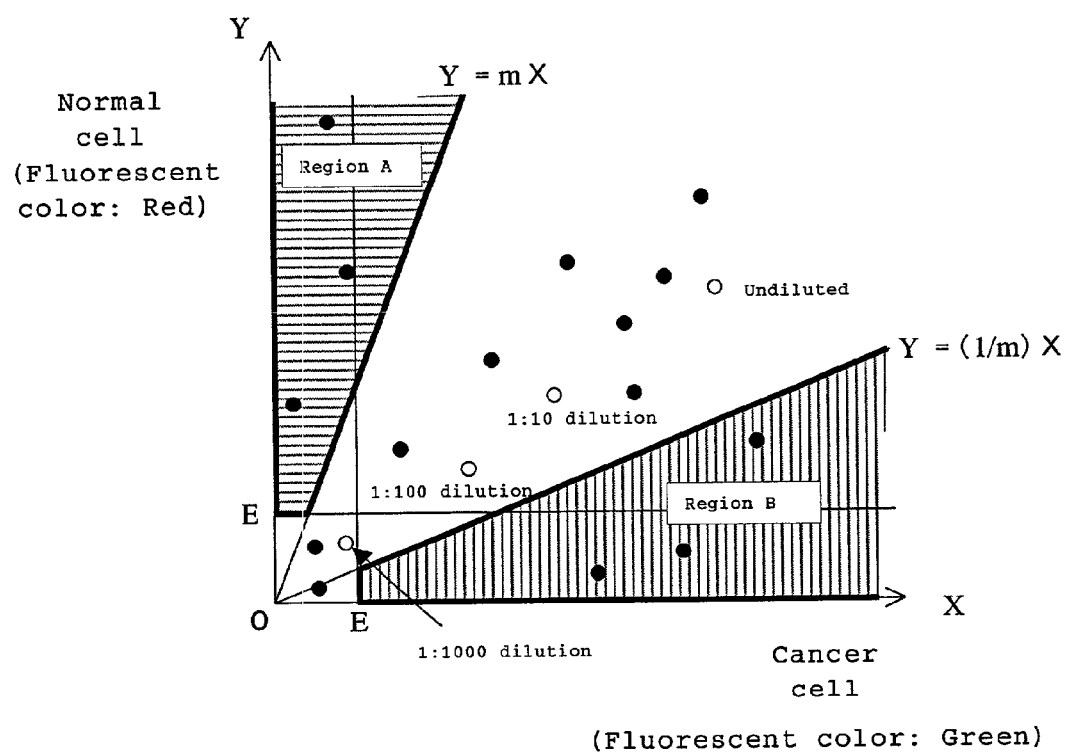
FIG. 3 is a schematic diagram illustrating an exemplary display (planar display) of results of a standard gene expression data analysis.

Next, the gene expression data is normalized (Step 201). FIG. 3 is a graph of one of the experiments obtained by plotting the measured values that are stored as data shown in FIG. 5. This is an exemplary display of the above-described standard gene expression data. In general, however, errors caused by an instrument, an experimental error caused upon such an error, or the like is included in the raw measured fluorescent brightness.

According to the present embodiment, a particular gene is spotted on a biochip for correcting the measured experiment values. This gene is referred to as a control and the measured value thereof is plotted on the graph as an open dot in FIG. 3. In FIG. 3, the control gene is diluted and used as additional controls, and data thereof are plotted as multiple points. In the present example, four points are plotted representing the measured values of undiluted control, $\frac{1}{10}$ dilution, $\frac{1}{100}$ dilution and $\frac{1}{1000}$ dilution of the control. Since a gene used as the control is known to exhibit a constant expression level both for a normal cell and for an abnormal cell, the points on the graph shown in FIG. 3 should be inclined by 45° at spaces consistent with the degrees of dilutions. Thus, the entire gene expression data obtained from the experiment is converted to rearrange the positions of these controls to be on a line inclined by 45°. This is carried out by combining rotation around the origin of the points with enlargement/reduction conversion. These steps are referred to as a normalization process. The results obtained by the normalization process are acquired as data having a structure similar to FIG. 5. The control data after the normalization is lined with an inclination of 45° as shown in FIG. 4.

Figure 4:
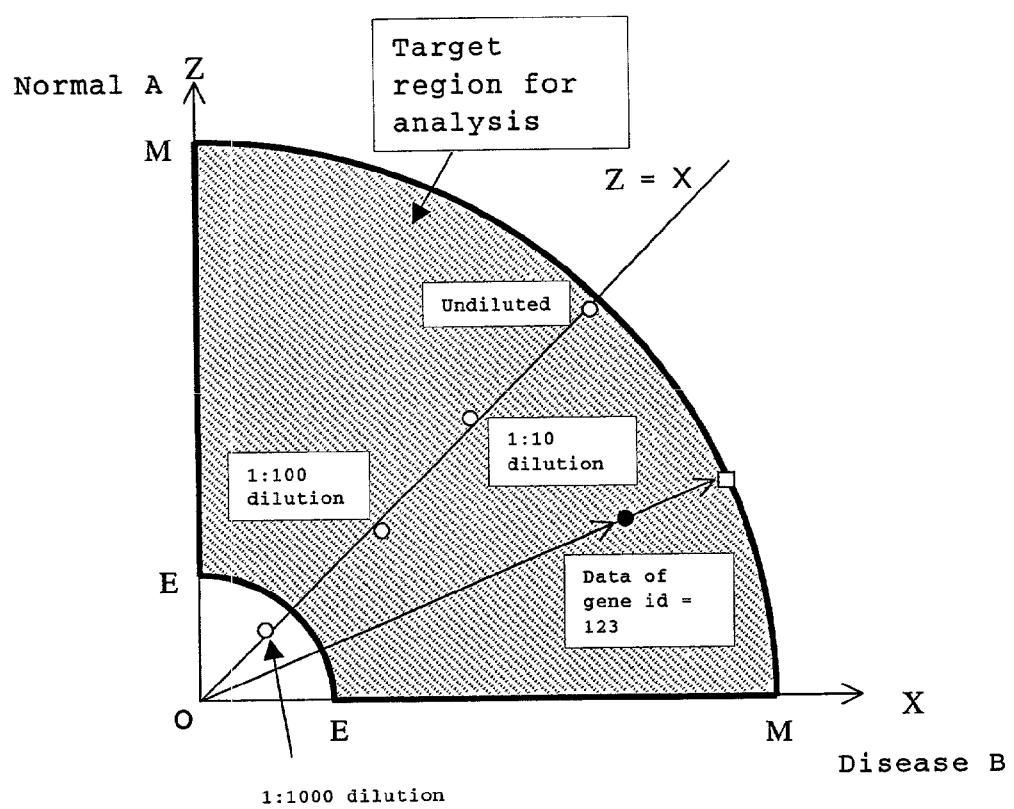
FIG. 4 is a diagram showing an example of determining a target region for expression data analysis.

Next, in the graph shown in FIG. 4 plotted with normalized gene expression data, a target region of gene expression data is determined for analysis (Step 202). Since some of the measured brightness may be too low or too high, the lowest and highest threshold values E and M are determined by the user. These thresholds are determined relative to the variation of the measured values in the normalized graph shown in FIG. 4. Since the results from the two experiments are simultaneously compared and displayed according to the present method, values common to both experiments are used. By determining the target region for analysis, only the experiment values that fall within a hatched sector shown in FIG. 4 excluding an area around the origin are subjected to subsequent processes such as displaying process.

The plots within the target sector region for analysis may be viewed in two ways. One way is to judge the state of gathering of plots in terms of distance of distribution within the region by comparing the absolute levels of fluorescent expression brightness of Normal cell A and Disease cell B. According to the present invention, this corresponds to a display method of plotting inside a sphere. The other way is to observe relative levels of the fluorescent expression brightness of the Normal cell A and Disease cell B. This is substantially the same, for example, as judging the states of gathering of plots by connecting between the origin and the plot (close dot) of gene data in FIG. 4 and extending the line to the great arc (open square). According to the present invention, this corresponds to a display method of plotting on a surface of a sphere.

Next, the gene expression data is converted to be displayed (Step 203). The data is converted by following a calculation for three-dimensional projection which conserves a relative ratio of expression brightness of each experiment. Specifically, coordinates for three-dimensional display are obtained for each gene by the following calculation based on the measured values in each experiment.

First, measured values from Experiment 1 (measured values of Normal cell A and Disease cell B) and measured values from Experiment 2 (measured values of Normal cell A and Disease cell C) are represented as (a, b) and (A, c), respectively. The two sets of measured values are converted into ratios where the measured value of the normal cell common to both set is 1. As a result, (1, b/a) and (1, c/A) are obtained, which are converted into three-dimensional coordinates (b/a, c/A, 1). The three-dimensional coordinates are enlarged or reduced in the radius direction. The magnitude of the enlargement R or reduction r in the radius direction for display inside a sphere or on a surface of a sphere of the invention are calculated by the following calculation. Herein, sqrtf{} refers to a function for calculating positive square roots.

$$r=sqrt\{(b/a)^2+(c/A)^2+1\}$$

$$R=sqrt\{(b^2+c^2+(a+A)^2)\}$$

By using r and R, the coordinates (x, y, z) are determined as follows.
(1) coordinates for display inside a sphere:
((R/r)(b/a), (R/r)(c/A), R/r)
(2) coordinates for display on a surface of a sphere:
((K/r)(b/a), (K/r)(c/A), K/r)
Where K in the above coordinates is a radius of the display sphere, which is a constant value for adjusting the display to be viewable through enlargement or reduction.

The two sets of coordinates obtained by the above-described calculations both conserve the ratios of expression levels obtained in Experiments 1 and 2. This may be confirmed by projecting the three-dimensional coordinates on an X-Z plane or a Y-Z plane. When the points given by the two sets of three-dimensional coordinates are considered with respect to the directional vector only, without the coefficient R/r or K/r for enlargement or reduction, it can be noted that the points lie on a line represented by a three-dimensional directional vector (b/a, c/A, 1). In order to project these points on the X-Z plane, the y-coordinate is set to zero, and thus coordinates (b/a, 0, 1) are obtained as the projection results. Since this is in the same direction as a directional vector (b, 0, a), the ratio between x- and z-coordinates is b to a, proving that the ratio between the measured values of Normal cell A and Disease cell B in Experiment 1 is conserved. Similarly, in order to project the points on the Y-Z plane, the x-coordinate is set to zero, and thus coordinates (0, c/A, 1) are obtained as the projection results. Since this is in the same direction as a directional vector (0, c, A), the ratio between z- and x-coordinates is c to A, proving that the ratio between the measured values of Normal cell A and Disease cell C in Experiment 2 is conserved.

The thus-obtained coordinates to be displayed inside a sphere obtained by the above-described calculation also conserve the magnitude relation between the expression levels obtained in Experiments 1 and 2. This means that, for example, for two measured values (a1, b1) and (a2, b2) obtained for two types of genes in Experiment 1 assuming that:
(1) the ratios of the expression levels, b1/a1 and b2/a2, are identical;
(2) a1 is lower than a2 (and thus b1 is lower than b2); and
(3) the two values (A1, c1) and (A2, c2) measured in Experiment 2 are substantially the same value, the points represented by the coordinates lie on the same line on the X-Z plane, where the projected points corresponding to (a1, b1) is closer to the origin. Because the ratio of the expression levels is conserved in the two projected points, they lie on the same line on the X-Z plane. The distance from the origin is defined by R/r. Since values r calculated for the two types of genes are the same based on the assumptions (1) and (3) above, the magnitude relation between the distances is defined by the values R. According to the calculation of R, the projected point corresponding to (a1, b1) is closer to the origin based on the above assumption (2).

Since an error due to the spotting amount occurs upon production of a biochip, the most reliable quantitative unit at present is the ratios of the expression levels. Accordingly, when results from multiple experiments are to be combined, it is very important that they are displayed while conserving their ratios. Since two-dimensional real projective plane is employed as the mathematical model, the display on a sphere of the invention is advantageous in that the distance between the two ratios for three experiment values can be compared by measuring the length of the arc of the great circle of the sphere.

Since the magnitude relation between the expression levels is biased upon combining the results from the two experiments, it is difficult to convert them into three-dimensional display while completely retaining the quantitativity. However, the order of the magnitudes can be maintained. The relation of the magnitudes of the expression levels reflects the observed intensities of the fluorescent luminescence resulting from a hybridization reaction, and thus, there should be a quantitative difference in a logarithmic order. Even such a rough difference is important and worthwhile storing considering its influence on the gene groupings upon the subsequent clustering analysis.

Figure 6:
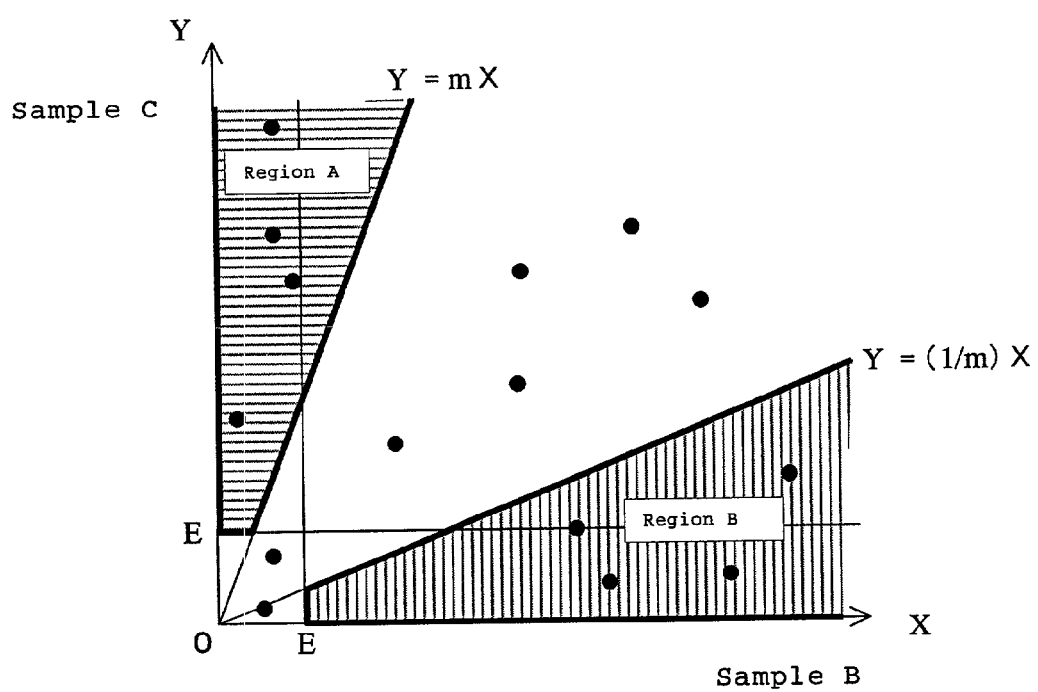
FIG. 6 is an exemplary display of gene expression data.
Figure 7:
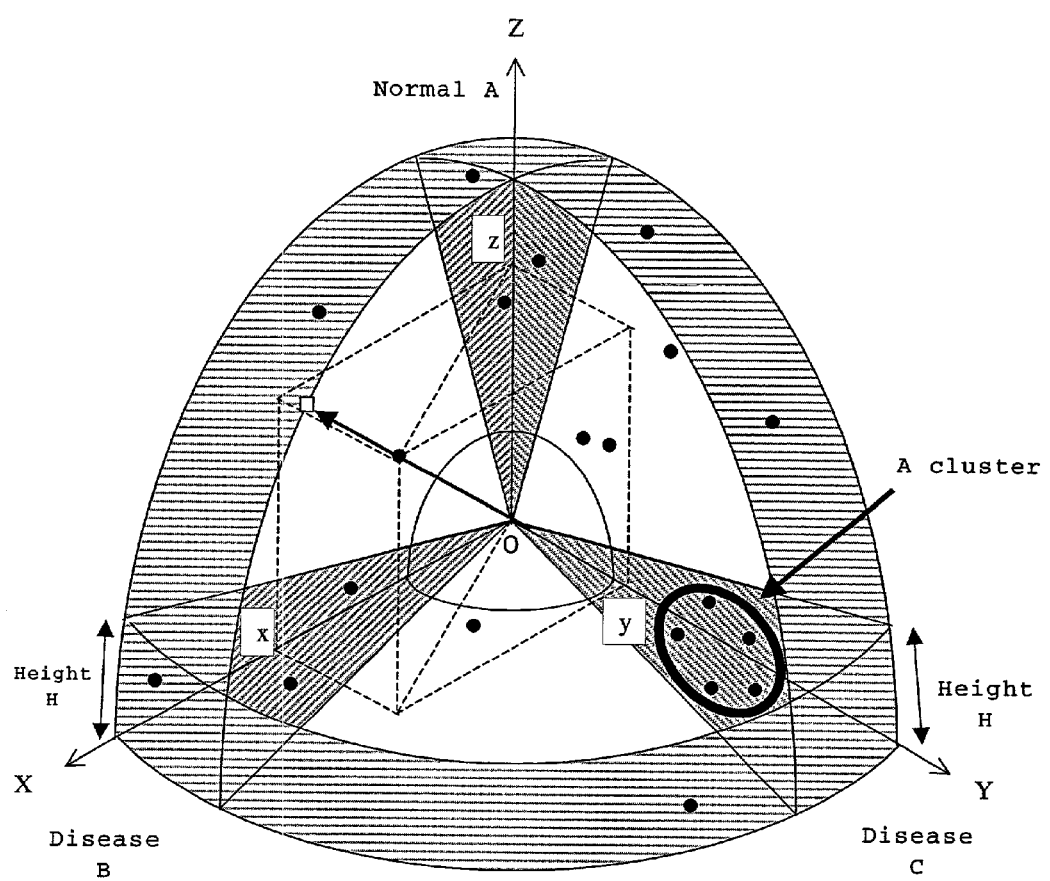
FIG. 7 is an exemplary display of gene expression data (inside a sphere).
Figure 8:
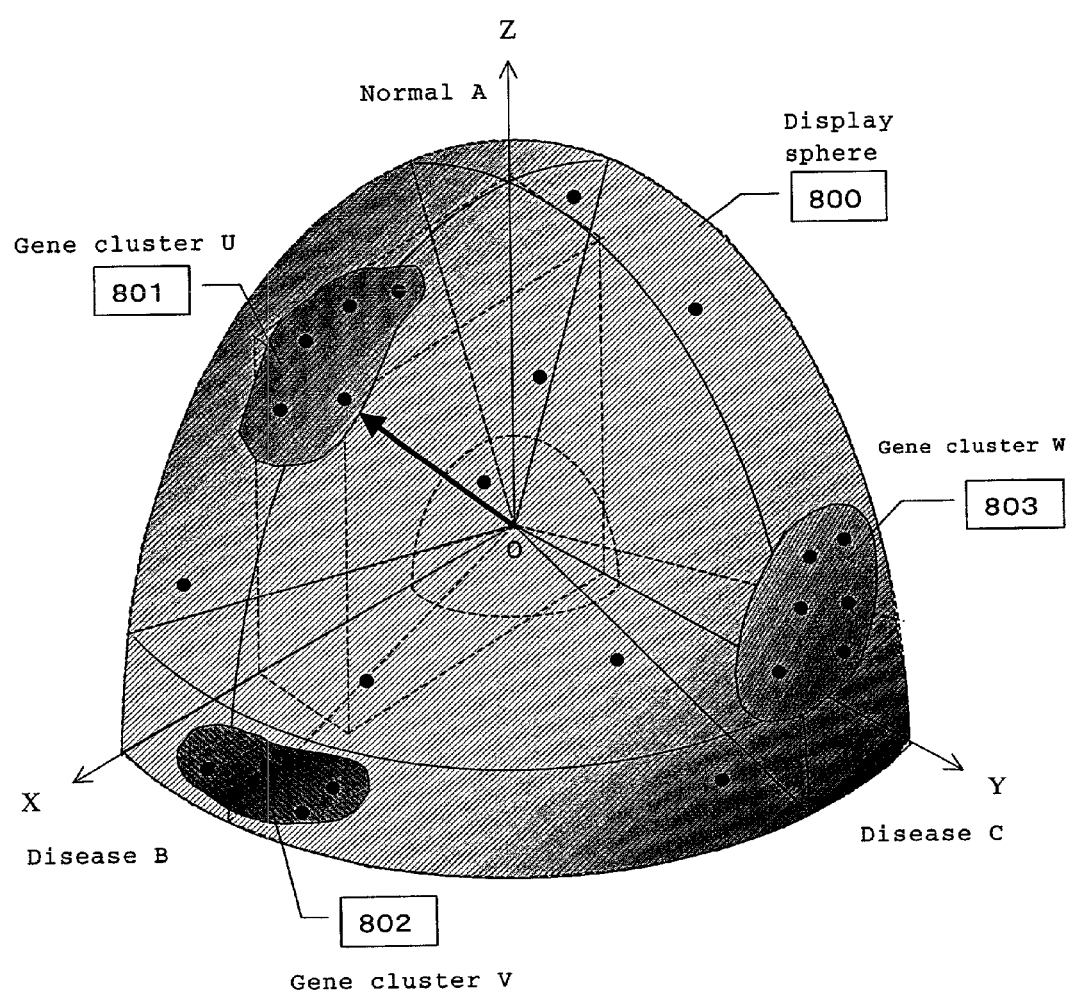
FIG. 8 is an exemplary display of gene expression data (on a surface of a sphere).
Figure 9:
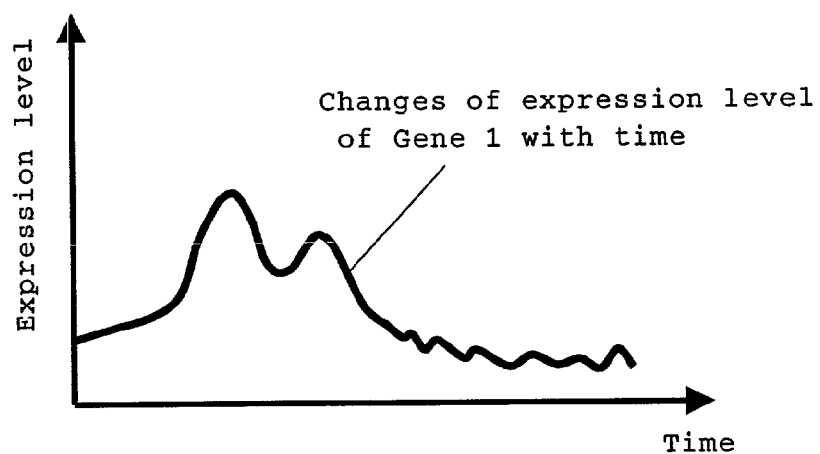
FIGS. 9A and 9B are exemplary graphs showing changes of standard gene expression data with time.
Figure 9:
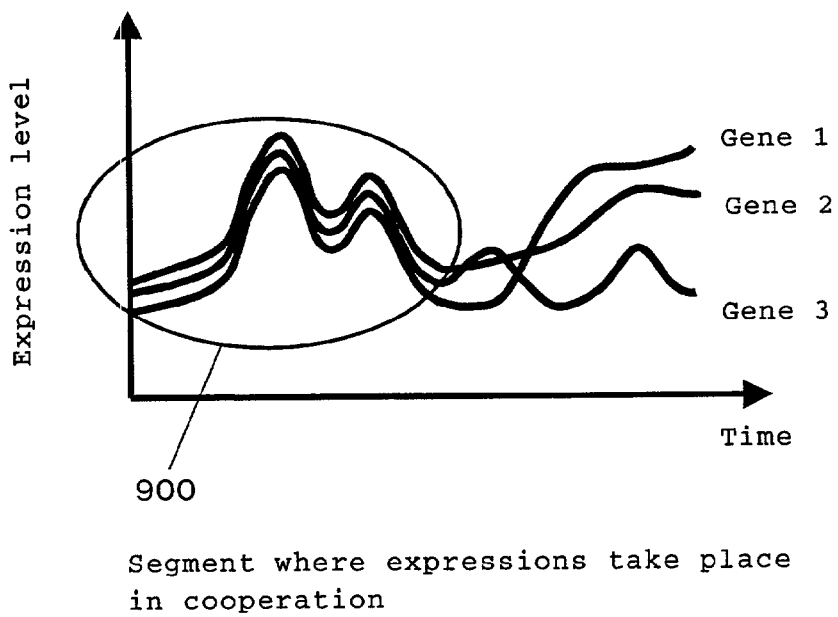

Next, by utilizing the above-described coordinates determined for three-dimensional display, the converted gene expression data is displayed (Step 204). Specifically, coordinates for each gene are calculated and plotted on a two-dimensional coordinate system consisting of x- and y-axes or a three-dimensional coordinate system consisting of x-, y-and z-axes. The data is plotted in a one-eighth semitransparent sphere or on a surface thereof, where all of x-, y- and z-axes have their origin at the center of the sphere. FIGS. 6, 7 and 8 show examples of such displays.

FIG. 6 is an exemplary display where experiment results for Samples A and B and experiment results for Samples A and C are combined and displayed for comparing gene expression levels of Samples B and C.

Although this graph is similar to the graph shown in FIG. 3, there is a great difference in that an experiment using a biochip is not performed for directly comparing Samples B and C. Only the x- and y-coordinates of the sphere coordinates are partially taken as coordinates for this planer display: ((R/r)(b/a), (R/r)(c/A)) are plotted on an x-y plane as (x, y).

The graph shown in FIG. 6 can be interpreted in the same manner as the graph shown in FIG. 3. Specifically, plots whose ratios of the expression levels between Sample B and C are higher than a predetermined value (Region A: above line Y=mX) or plots whose ratios are lower than a predetermined value (Region B: below line Y=(1/m)X) can be predicted to be the expression data representative of genes that serve specific to either Sample B or C.

FIG. 7 is an exemplary three-dimensional display of gene expression data plotted inside a semi-transparent sphere. The hatched spatial region corresponds to Regions A and B shown in FIG. 3, where genes that serve specific to Normal cell A and Disease cells B and C can be observed. Noteworthy, although the present embodiment does not perform an experiment for directly comparing Disease cells B and C, the experiment results for Samples A and B and the experiment results for samples A and C are combined and displayed as shown in FIG. 7. Thus, candidate genes that behave specific to Disease B or C, or to both of them can visually be observed and sorted. FIG. 8 is an exemplary display where the gene expression data are plotted on a surface of a sphere.

Returning to FIG. 2, at last, the displayed gene expression data is subjected to a clustering analysis, and the obtained cluster regions are displayed inside or on the sphere (Step 205). FIGS. 7 and 8 schematically show plotting inside and on the sphere, respectively, and the results of the subsequent clustering analysis. The clustering analysis here refers to a hierarchy algorithm employed in a general multivariate analysis. For example, in the case of plotting on the sphere as shown in FIG. 8, a distance between two plots is measured as a distance on the surface of the sphere (a length of an arc of the great circle linking the two points) based on the ratio of the expression levels conserved from the results from the two original experiments. Any algorithm can be employed for cluster joining such as Ward method, group average method, nearest neighbor method, furthest neighbor method, centroid method and median method. In FIG. 8, Cluster V of genes that function specific for Disease cell B but not for the normal cell and Cluster W of genes that function specific for Disease cell C but not for the normal cell are detected.

By following the processes of the flowchart shown in FIG. 2, from the experiment results for Samples A and B and those for Samples A and C, gene expression levels of Samples B and C can be displayed and compared as shown in FIG. 6, or gene expression data and results of a clustering analysis can be plotted inside a sphere or on a sphere as shown in FIGS. 7 and 8, respectively. In the above-described three-dimensional display, the viewing direction of a user can be controlled with a mouse or the like by rotating or shifting the x-y-z-coordinate system to position the detected cluster to a prominent position for confirmation.

In order to study changes of gene expression in a time series of the gene, experiments may be carried out at respective time points using biochips and display the expression data for each gene in a time series to study the change in a plurality of genes. In this case, the above-described display on the surface of or inside the sphere is repeated, and the displayed plots are linked, thereby displaying course of changes with time on or inside the sphere.

Figure 10:
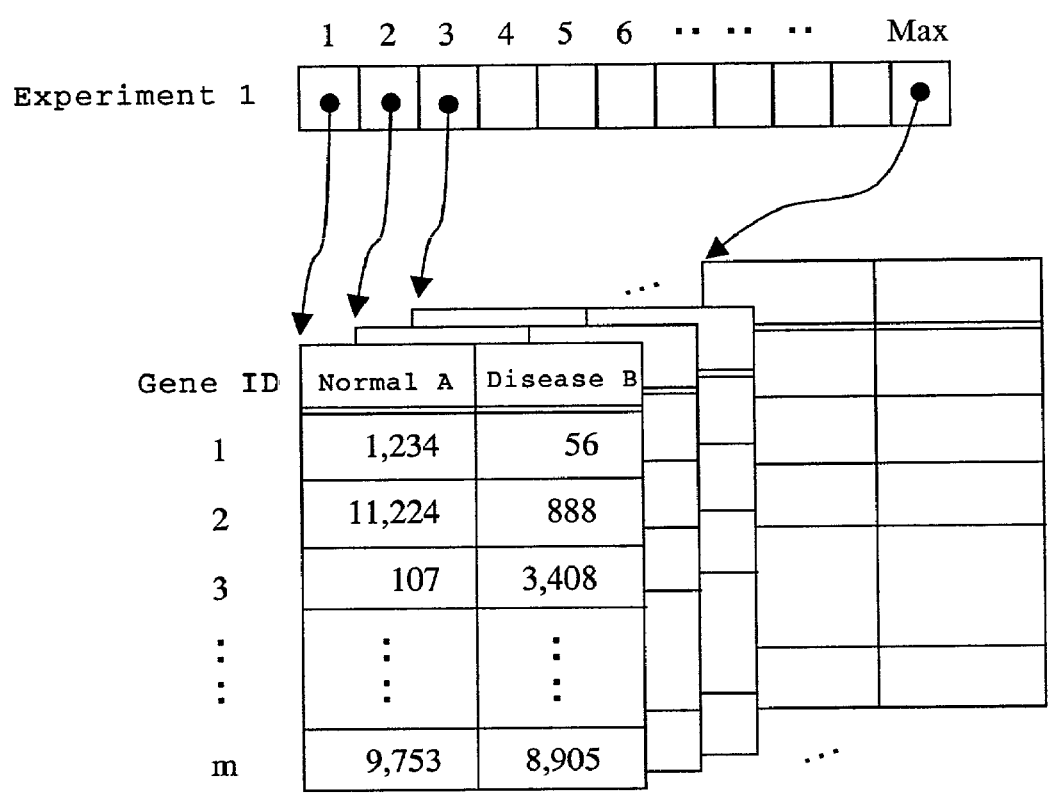
FIG. 10 is a specific example of data from gene expression experiments carried out in a time series.

FIG. 10 is a diagram showing exemplary expression data from Experiment 1 shown in FIG. 5 accumulated in a time series. Herein, elements of a sequence whose data structure corresponds to Experiment 1 store data obtained at constant intervals (e.g., at hour intervals or week intervals).

In order to draw a line or a curve to display the changes of expression data with time, the processes are repeated while successively altering the index of the sequence shown in FIG. 10 to fetch the brightness of the fluorescent color stored in the data corresponding to each element, to determine the display positions on or inside the sphere and draw an arrow or an interpolated curve between the displayed positions. The plurality of genes may be captured as a gene group via the above-described clustering analysis. In this case, a state of changes may be drawn as travel, division and joining of the gene groups.

The displaying procedure according to the flowchart shown in FIG. 2 is repeated for each index of the sequence. Alternatively, instead of repeating the entire process shown in FIG. 2 for each time point, a part of the procedure such as the data reading out process and data normalization process of Steps 200 and 201 may be carried out at once, and thereafter the results may be displayed.

Figure 11:
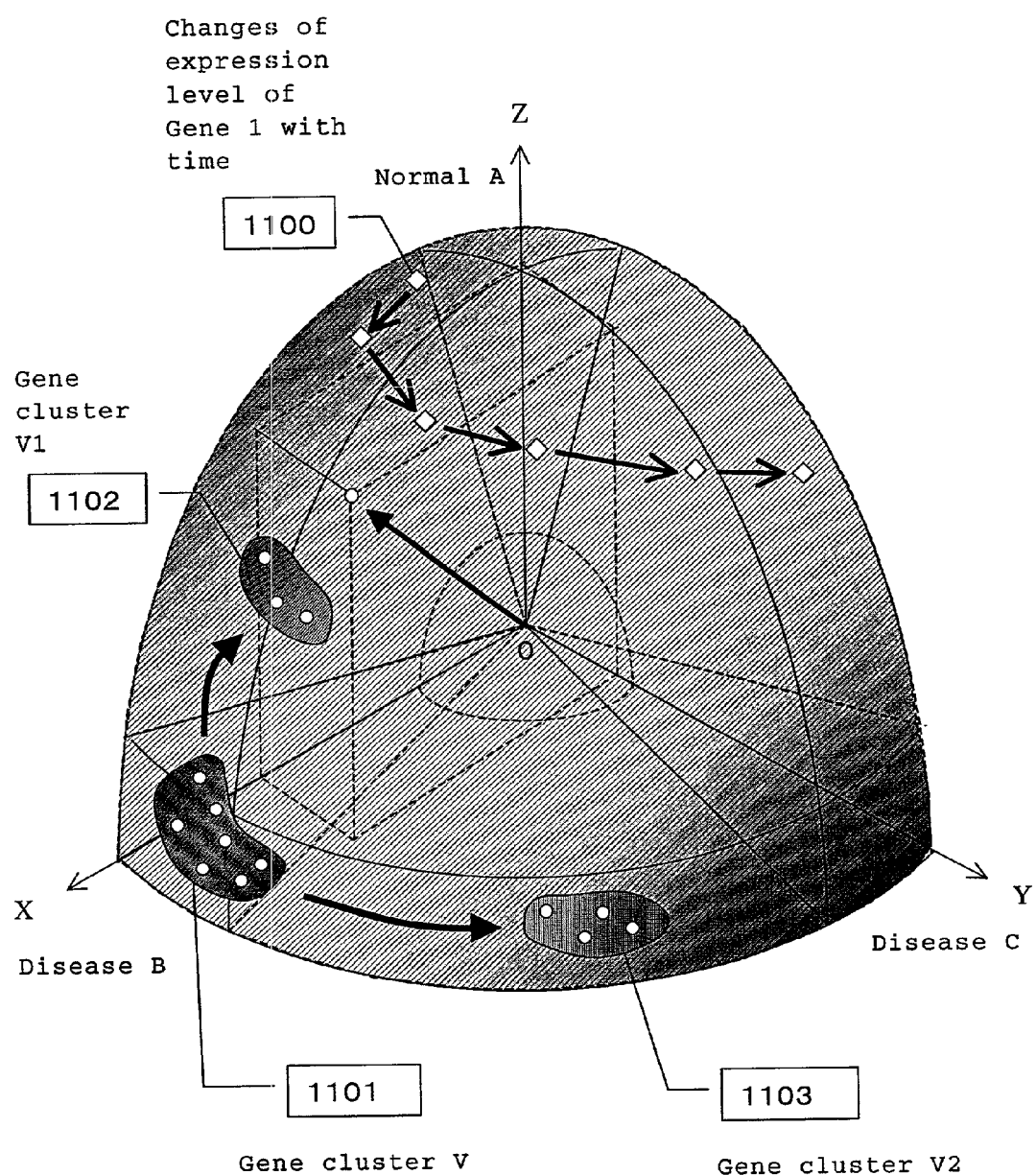
FIG. 11 is an exemplary display showing changes of the gene expression data with time (on a surface of a sphere).

FIG. 11 is an exemplary display showing changes of gene expression data with time on the surface of the above-described sphere.

Display 1100 traces changes of expression of a single gene (Gene 1) with time by successively calculating the expression data of the gene and linking the displayed positions thereof by arrows. In this example, one can assume that Gene 1 which is initially strongly expressed in Normal cell A becomes to be expressed in a cell suffering from Disease C in a delayed manner.

Display 1101 is Gene cluster V calculated in the above-described clustering analysis and displayed on the sphere, which in time is divided into two groups, Gene cluster V1 (1102) and Gene cluster V2 (1103) as shown in FIG. 11. This is represented by curved arrows linking partial regions on the sphere. In this example, one can assume that the gene group which is initially strongly expressed in Disease cell B is divided into two groups, one also functioning in Normal cell A but little in Disease cell C and the other also functioning in Disease cell C but little in Normal cell A.

Figure 12:
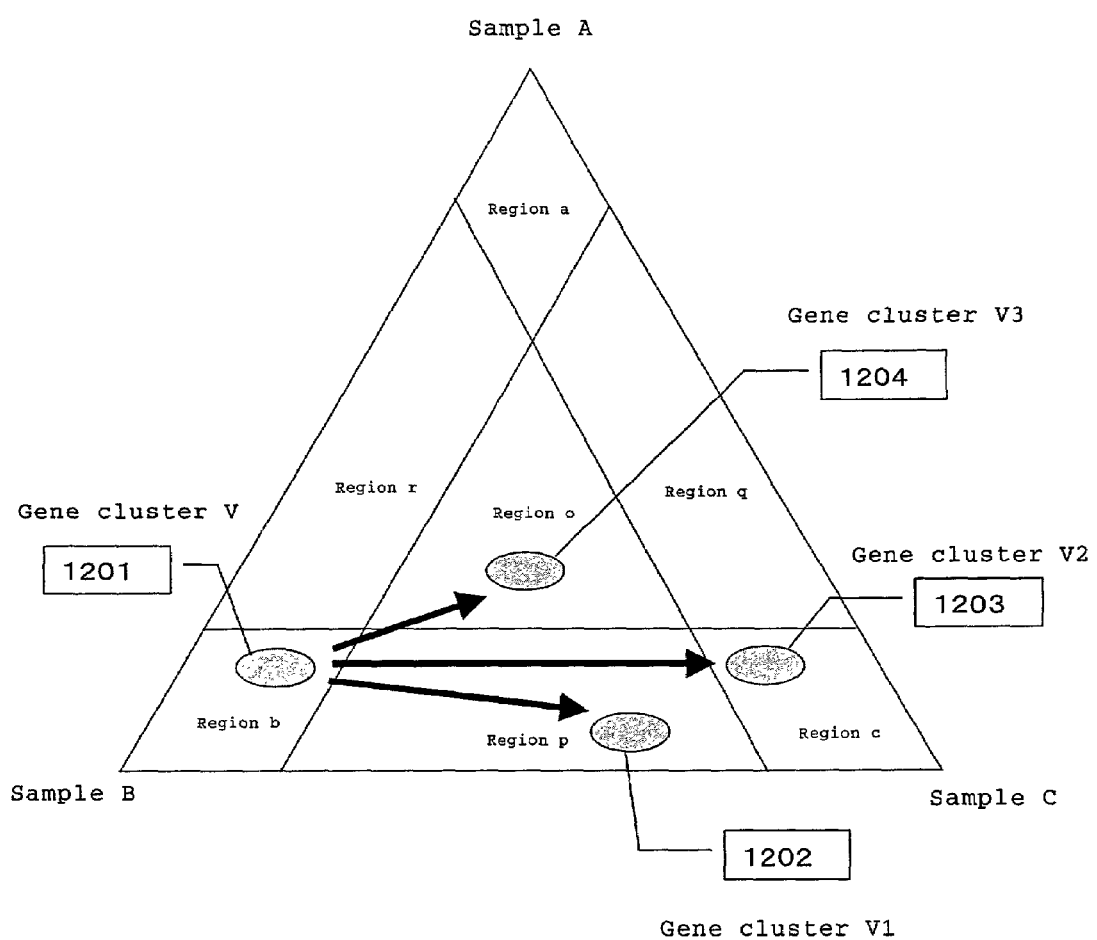
FIG. 12 is a schematic illustration as to interpretation of the display of the changes of the gene expression data with time (on a surface of a sphere).

FIG. 12 is a schematic diagram for illustrating an interpretation of changes of gene expression data displayed on the sphere with time. The one-eighth sphere region shown in FIG. 11 is converted into a triangle such that each constituent region of the sphere are considered as each constituent region of the triangle. For example, a rhombus region a at the upper part of the triangle corresponds to the uppermost region with respect to the z-axis of the sphere shown in FIG. 11.

Travel of displayed positions of a gene expression or a gene group across the regions of the triangle is interpreted as changes of gene expression with time, from which changes of the function of the gene may be predicted. For example, when Gene cluster V (1201) initially displayed in Region b transfers to Regions p and c as Gene clusters V1 (1202) and V2 (1203), respectively, one can assume that the gene group of interest initially had a significant expression level in Sample B, but its expression level in Sample C gradually became higher. On the other hand, when Gene cluster V (1201) transfers to Region o and displayed as Gene cluster V3 (1204), one can assume that the gene group of interest initially had a significant expression in Sample B but thereafter the expression is equalized among Samples A, B and C.

Figure 13:
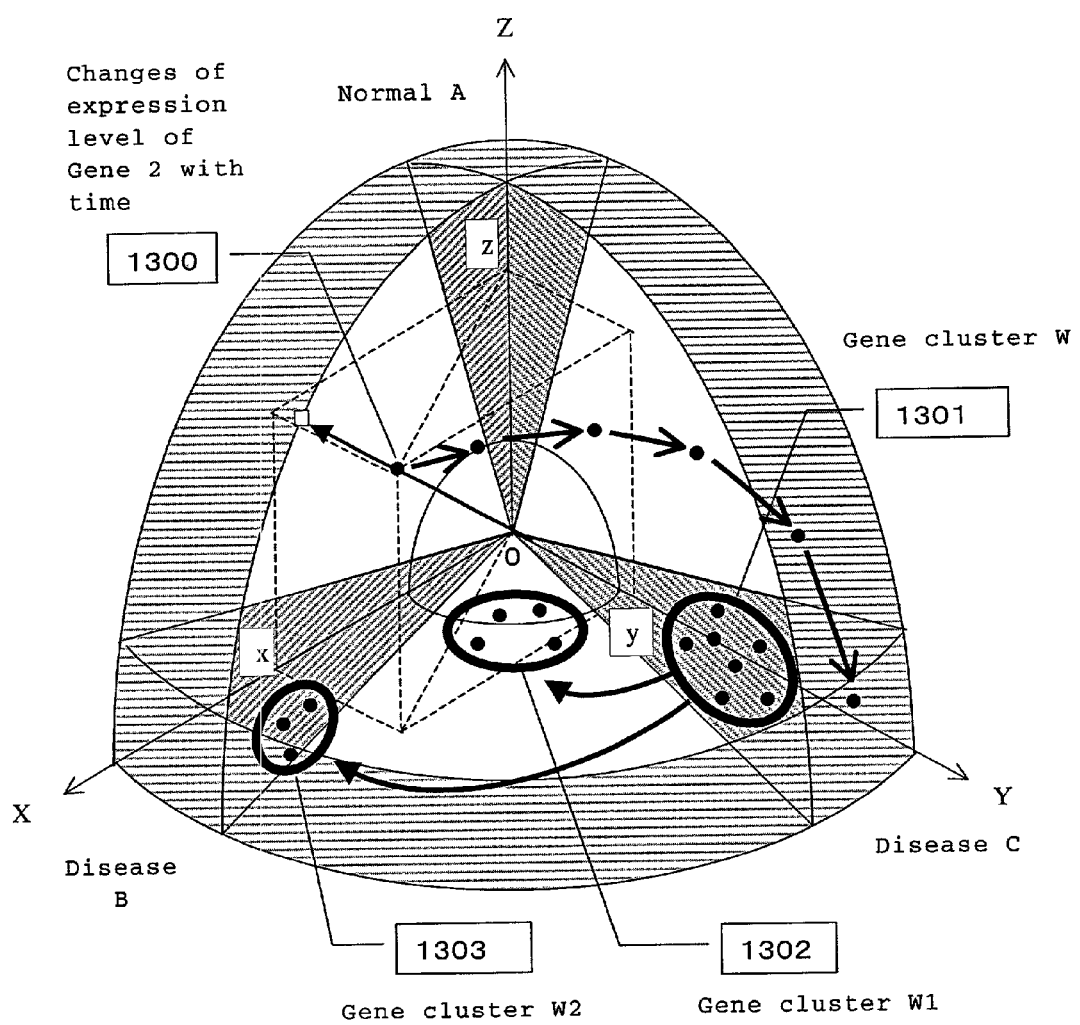
FIG. 13 is an exemplary display showing changes of the gene expression data with time (inside a sphere).

FIG. 13 is an exemplary display showing changes of gene expression data with time inside the above-described sphere.

Display 1300 traces changes of expression of a single gene (Gene 2) with time by successively calculating the expression data of Gene 2 and linking the displayed positions by arrows. In this example, one can assume that Gene 2 which is initially moderately expressed in Normal cell A and a cell suffering from Disease B becomes to exhibit weaker expression in Cells A and B but particularly strongly in a cell suffering from Disease C.

Display 1301 is Gene cluster W calculated in the above-described clustering analysis and displayed inside the sphere, which in time is divided into two groups, Gene cluster W1 (1302) and Gene cluster W2 (1303) as shown in FIG. 13. This is represented by curved arrows linking partial regions inside the sphere. In this example, one can assume that the gene group which is initially moderately expressed in Disease cell C is divided into two groups, one hardly expressed in Normal cell A and less than moderately expressed in Disease cells B and C, and the other expressed higher in Disease cell B but hardly in Normal cell A and Disease cell C.

Specific experiments to which these display methods can be applied may be, for example, the following experiments which may be carried out to study changes of gene expression level with time.

(i) Experiment for comparing patients with predisposition types A, B and C with respect to an incidence of suffering from Disease X.

(ii) Experiment for comparing Strains A, B and C with respect to activity states of a microorganism (such as bacteria).

(iii) Experiment for comparing expression states of a plurality of genes at three sites (such as head, torso and limbs) during the course of development of particular species.

(iv) Experiment for detecting differences in gene expressions in three types of organs (such as liver, kidney and heart).

According to the present displaying method, for example, B and C can be compared by simply observing changes, in experiment for A and B, and an experiment for A and C, with time and collecting data therefrom. Since an experiment for comparing B and in a time series can be omitted, experiment labor can be reduced.

As described above, from the experiment results of Samples A and B, and those of Samples A and C observed in a time series, plots of gene expression data and results of a clustering analysis thereof in a time series can be displayed on a sphere as shown in FIG. 11, or they can be displayed inside a sphere as shown in FIG. 13. Thus, gene functions of a plurality of genes with respect to changes with time can be predicted.

According to the present invention, based on expression data of one gene resulting from two experiments, expression data of other genes can be compared and visually displayed inside or on a sphere, which is effective for roughly understanding the state of groupings and changes.

What is claimed is:

1. A method for displaying gene expression data in comparing gene expression levels of a plurality of genes found in different Samples A, B, C, comprising:
   calculating a first ratio b/a of a gene expression level b of one of said plurality of genes for the Sample B with respect to a gene expression level a of said one of said plurality of genes for the Sample A for each of said plurality of genes in a first experiment;
   calculating a second ratio c/A of a gene expression level c of said one of said plurality of genes for the Sample C with respect to a gene expression level A of said one of said plurality of genes for the Sample A for said each of said plurality of genes in a second experiment;
   obtaining a dataset of gene expression levels for the Samples B, C, A expressed as (b/a, c/A, 1) for said each of said plurality of genes;
   calculating a first magnitude r of said dataset expressed as $r = \sqrt{\{(b/a)^2 + (c/A)^2 + 1\}}$; and
   displaying a mark of a first product of the first ratio and K/r, a second product of the second ratio and the K/r, and the K/r on a coordinate position with respect to x-, y- and z-axes on a surface of a sphere for said each of said plurality of genes, K being a radius of the sphere, to thereby compare gene expression levels of said plurality of genes found in the samples A, B, C.

2. A method for displaying gene expression data according to claim 1, further comprising: calculating a second magnitude R of said dataset expressed as $R = \sqrt{\{(b^2 + c^2 + (a+A)^2)\}}$ displaying a mark of a third product of the first ratio and R/r, a fourth product of the second ratio and the R/r, and the R/r on a coordinate positions with respect to x-, y- and z-axes for said each of said plurality of genes.

3. A method for displaying gene expression data according to claim 2, further comprising: performing a clustering analysis on the displayed magnitude coordinate positions inside the sphere for said plurality of genes; and marking at least one gene group obtained by the clustering analysis as a region inside the sphere.

4. A method for displaying gene expression data according to claim 3, wherein the expression level data is data in a time series, and said region is displayed based on respective time points in conjunction with a direction of changes of said region with time in the displaying step.

5. A method for displaying gene expression data according to claim 2, wherein the expression level data is data in a time series, which is displayed based on respective time points for said each of said plurality of genes in conjunction with a direction of changes of the coordinate positions with time in the displaying step.

6. A method for displaying gene expression data according to claim 1, further comprising: performing a clustering analysis on the displayed marks for said plurality of genes on the sphere; and marking at least one gene group obtained by the clustering analysis as a region on the sphere.

7. A method for displaying gene expression data according to claim 6, wherein the expression level data is data in a time series, and said region is displayed based on respective time points in conjunction with a direction of changes of said region with time in the displaying step.

8. A method for displaying gene expression data according to claim 6, wherein the expression level data is data in a time series, which is displayed based on respective time points for said each of said plurality of genes in conjunction with a direction of changes of the coordinate positions with time in the displaying step.

9. A method for displaying gene expression data according to claim 1, wherein the expression level data is data in a time series, which is displayed based on respective time points for said each of said plurality of genes in conjunction with a direction of changes of the coordinate positions with time in the displaying step.

* * * * *